(12) United States Patent
Lee

(10) Patent No.: US 9,248,045 B2
(45) Date of Patent: Feb. 2, 2016

(54) DISPENSING SYSTEM

(71) Applicant: Line One Laboratories Inc. (USA), Chatsworth, CA (US)

(72) Inventor: Budiman Lee, Chatsworth, CA (US)

(73) Assignee: Line One Laboratories Inc. (USA), Chatsworth, CA (US)

( * ) Notice: Subject to any disclaimer, the term of this patent is extended or adjusted under 35 U.S.C. 154(b) by 0 days.

(21) Appl. No.: 14/191,148

(22) Filed: Feb. 26, 2014

(65) Prior Publication Data

US 2014/0174961 A1    Jun. 26, 2014

Related U.S. Application Data

(63) Continuation of application No. 13/557,396, filed on Jul. 25, 2012, now abandoned, which is a continuation-in-part of application No. 13/230,602, filed on Sep. 12, 2011, now Pat. No. 8,256,609.

(51) Int. Cl.
    *B65D 85/08*  (2006.01)
    *A61F 6/04*   (2006.01)
    *A61F 6/00*   (2006.01)

(52) U.S. Cl.
    CPC .. *A61F 6/005* (2013.01); *A61F 6/04* (2013.01)

(58) Field of Classification Search
    USPC .......................................................... 206/69
    See application file for complete search history.

(56) References Cited

U.S. PATENT DOCUMENTS

| 5,005,695 | A  | * | 4/1991  | Tennefos et al. ................ 206/69 |
| 5,046,618 | A  | * | 9/1991  | Wood ............................ 206/532 |
| 5,175,142 | A  |   | 12/1992 | Dervieux |
| 5,287,961 | A  | * | 2/1994  | Herran ......................... 206/219 |
| 6,076,661 | A  | * | 6/2000  | Abadi ............................ 206/69 |
| 6,287,652 | B2 | * | 9/2001  | Speckhals et al. ........... 428/35.2 |
| 6,338,407 | B2 | * | 1/2002  | Danville ....................... 206/532 |
| 8,256,609 | B1 | * | 9/2012  | Lee ............................... 206/69 |
| 8,851,284 | B2 | * | 10/2014 | Arefieg ........................ 206/390 |
| 2003/0141218 | A1 | * | 7/2003 | Stephens et al. ............. 206/820 |
| 2003/0226567 | A1 | * | 12/2003 | McCleskey et al. .......... 128/844 |
| 2004/0256274 | A1 | * | 12/2004 | Betsch ......................... 206/484 |
| 2005/0045497 | A1 | * | 3/2005 | Sample ........................ 206/69 |

FOREIGN PATENT DOCUMENTS

| CH | 693504 A5    | 9/2003 |
| JP | 2010168082 A | 8/2010 |
| WO | 9502379 A1   | 1/1995 |

OTHER PUBLICATIONS

Second Office Action, issued on Nov. 27, 2013, in Chinese Patent Application No. 201110451650.4.
European Search Report Application No. EP11009043 dated Feb. 7, 2013.

(Continued)

*Primary Examiner* — Jacob K Ackun
(74) *Attorney, Agent, or Firm* — Laura M. Lloyd; Katherine B. Sales; Leech Tishman fuscaldo & Lampl

(57) ABSTRACT

A dispensing system comprising a sealed package, no greater than 0.3 inches thick, connected together to form a rectangular sheet, a lubricant compartment having a first and a second sub-compartment and a prophylactic compartment.

15 Claims, 3 Drawing Sheets

(56) References Cited

OTHER PUBLICATIONS

First Office Action, issued on Jul. 22, 2013, in Chinese Patent Application No. 201110451650.4.

Lee, Budiman, First Office Action issued by the State Intellectual Property Office of China on Jun. 27, 2012 in corresponding Chinese Patent Application No. 201120564282.X filed Dec. 29, 2011 (with English translation).

* cited by examiner

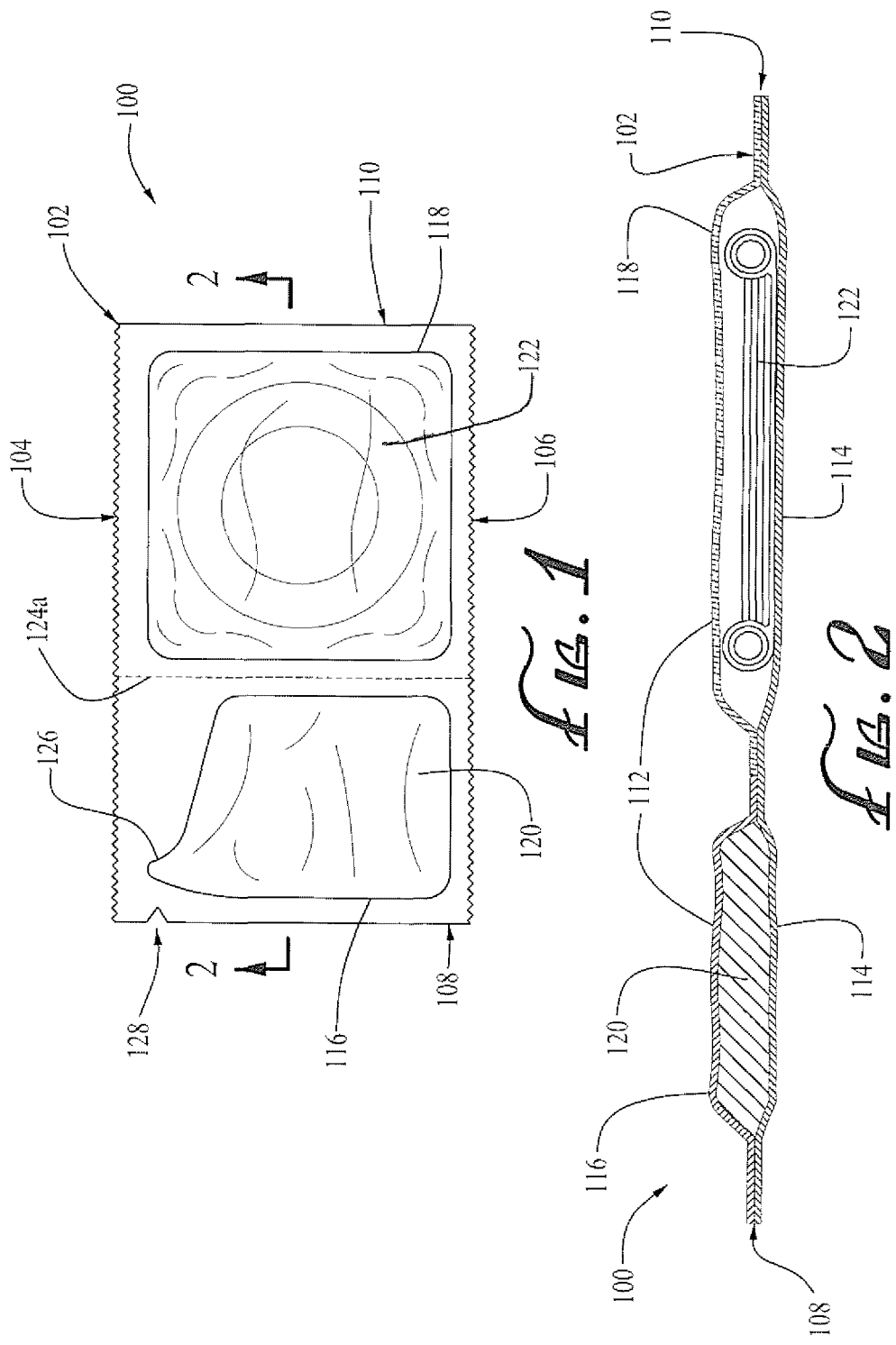

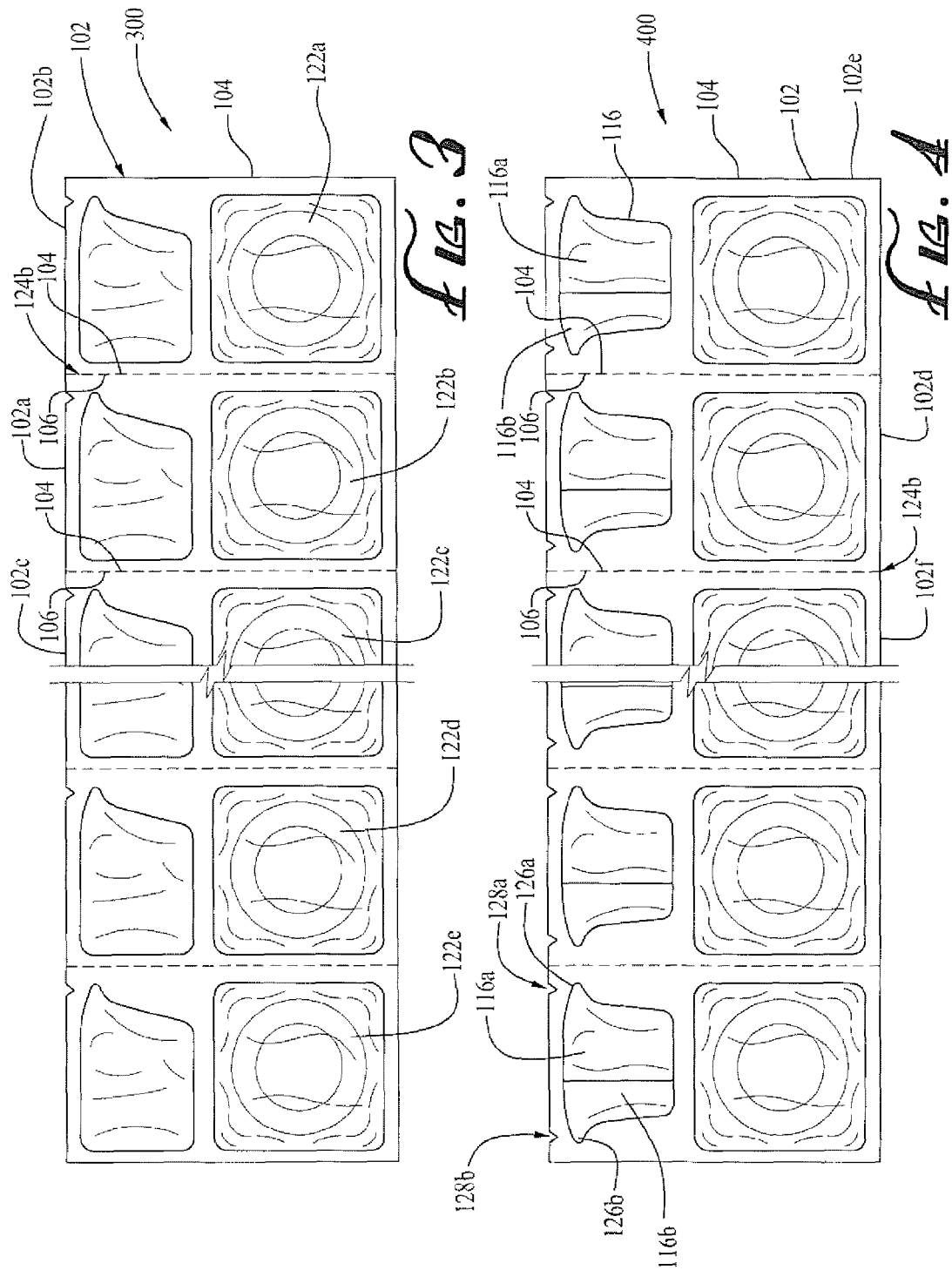

DISPENSING SYSTEM

CROSS-REFERENCE TO RELATED APPLICATION

The present Application is a continuation of U.S. patent application Ser. No. 13/557,396 titled "Dispensing System", filed on Jul. 25, 2012, which is a continuation-in-part of U.S. patent application Ser. No. 13/230,602 titled "Dispensing System", filed Sep. 12, 2011, the contents of which are incorporated in this disclosure by reference in their entirety.

BACKGROUND

Prophylactic and lubricants are commonly used during sex. Prophylactics are used for birth control and disease prevention purposes. Lubricants are commonly used for massages, and also for comfort, particularly with women past menopause.

Prophylactics are commonly dispensed through drugstores and through vending machines. Lubricants are commonly dispensed in containers containing much larger quantities of lubricant than needed at any single time, which is inconvenient to carry such as in a wallet, commonly used by men for carrying prophylactics. One exception to this is pre-lubricated prophylactics. A disadvantage of pre-lubricated prophylactics is that it is not possible to use the lubricant separately from the prophylactic, such as for massage or foreplay.

A problem associated with having separate dispensing systems for prophylactics and lubricants is that only one may be available when both are needed, and accessing those can be inconvenient and mood-destroying at the time of need.

Accordingly, there is a need for a better dispensing system for providing access to lubricant and prophylactics.

SUMMARY

The present invention is directed to such a dispensing system, and in particular, a device is provided in the form of a sealed package having a front wall, a rear wall, a lubricant compartment, and a prophylactic compartment. A lubricant is in the lubricant compartment and a prophylactic is in the prophylactic compartment. Thus both items are available in a single sealed package which can be provided and sold as a single unit, such as in dispensing machines.

Preferably, the lubricant compartment is trapezoidally shaped.

Preferably the front wall of the sealed package is substantially transparent so that users can easily view the contents of the package, and be sure to open the right compartment at the right time.

The front wall of the sealed package preferably is formed of burstable polyester film, with the rear wall of the sealed package substantially opaque, such as being formed of aluminum.

For access to the compartments of the sealed package so the compartments can be easily opened by hand without a tool, one or more weakened sections can be provided.

To control dispensing of the lubricant, preferably the lubricant compartment comprises a neck providing a narrow dispensing section. Optionally the lubricant compartment can have two or more sub-compartments, each having such a neck, and one of the sub-compartments can contain a germicide. So that one compartment can be separated from the other compartment, there can be perforations therebetween. Typically, the compartments are side by side, and can be adjoining.

In one form of the invention, a plurality of sealed packages are provided connected together in the form of a substantially rectangular sheet of a sufficient number so that at least one of the sealed packages is a mid package connected to at least two adjoining packages. For example, a mid package can be connected at its top edge to a first adjoining package at the bottom edge of the first adjoining package, and the mid package can be connected at its bottom edge to a second adjoining package at the top edge of the second adjoining package. Alternatively, the mid package can be connected at its first side edge to a first adjoining package at one of its side edges, and at its second side edge to a second adjoining package at one of the side edges of the second adjoining package.

In multipackage configurations, the sealed packages can be separated by perforations so that each sealed package can be stripped off one at a time.

Preferably the prophylactics are of different colors. This is particularly useful when different types or different sizes of prophylactics are provided, so that colors can be used for color coding.

DRAWINGS

These and other features, aspects and advantages of the present invention will become better understood with regard to the following description, appended claims, and accompanying figures where:

FIG. 1 is a front elevation view of a first version of a dispensing system according to the present invention comprising a sealed package;

FIG. 2 is a sectional view of the package of FIG. 1 taken along line 2-2 in FIG. 1;

FIG. 3 is a front elevation view of a second version of a dispensing system according to the present invention comprising a plurality of the sealed packages of FIG. 1 secured to each other;

FIG. 4 is a front elevation view of a third version of the invention; and

DESCRIPTION

Figure 5:
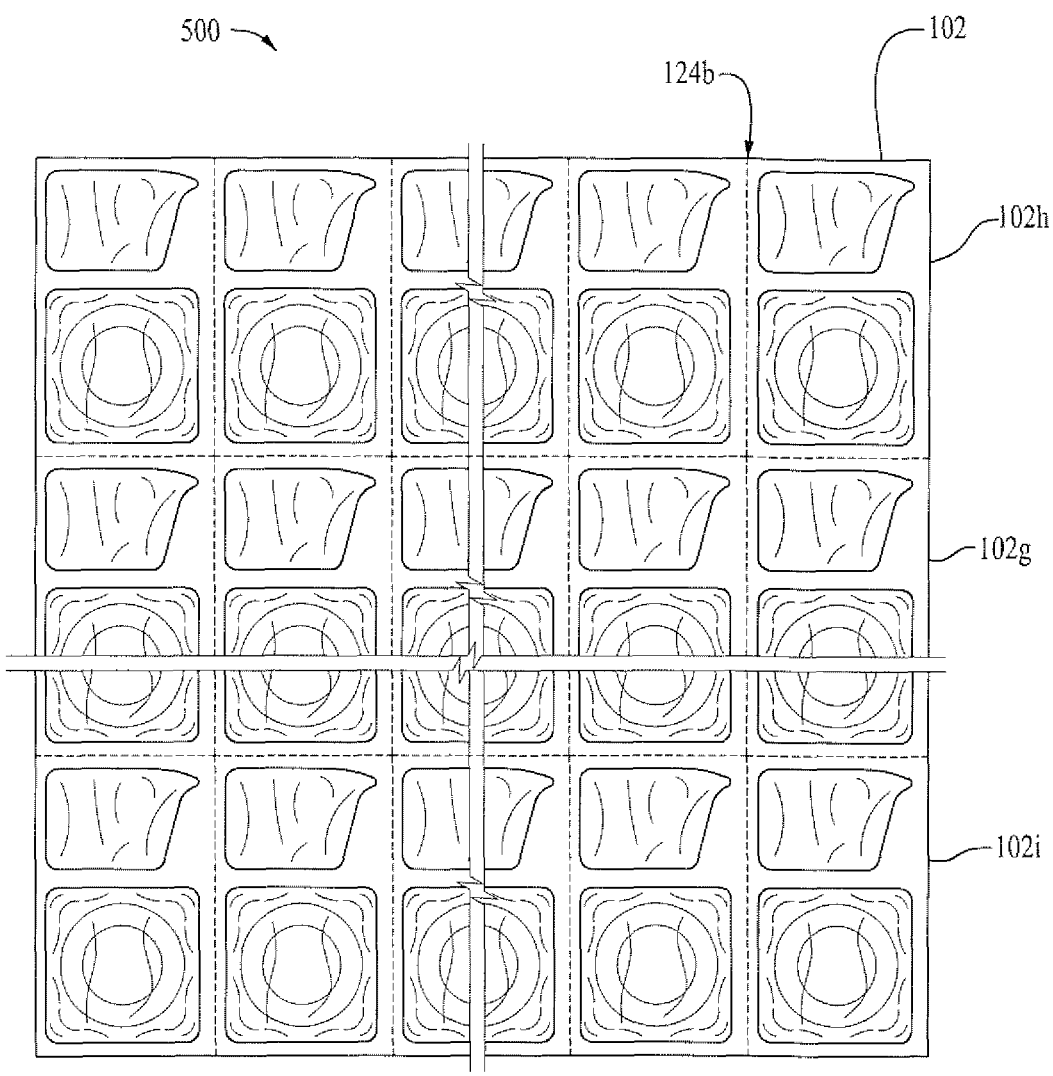
FIG. 5 is a front elevation view of a fourth version of the invention.

Referring now to FIGS. 1 and 2, a dispensing system 100 according to the present invention comprises a sealed package 102 having a top edge 104, a bottom edge 106, a first side edge 108, a second side edge 110, a front wall 112, a rear wall 114, a lubricant compartment 116, and a prophylactic compartment 118. The top edge 104 and bottom edge 106 can be ridged, smooth, or any other shape. Either or both compartments 116, 118 can be burstable, i.e. able to be burst open by the application of external pressure by hand. Generally only the prophylactic compartment 118 is burstable. Preferably, the sealed package 102 is dimensioned to fit into a user's wallet. The wallet can be a standard flat folding pocketbook that is large enough to hold paper money, credit cards, driver's licenses, etc.

The lubricant compartment 116 contains a lubricant 120, and the prophylactic compartment 118 contains a prophylactic 122. The thickness of the lubricant compartment 116 typically is about 0.1 inches when containing the lubricant 120, and the thickness of the prophylactic compartment typically is about 0.2 inches when containing the prophylactic 122. The prophylactic 122 can be a condom of any size, shape, or color, including but not limited to, lubricated, non-lubricated, ribbed, scented, flavored, or colored condoms. The lubricant compartment 116 can be located side-by-side with the prophylactic compartment 118 or in any other arrangement that allows both the lubricant compartment 116 and the prophylactic compartment 118 to fit without overlapping in the sealed package 102. There can be perforations 124a separating the lubricant compartment 116 from the prophylactic compartment 118 so that the lubricant compartment 116 can be stripped from the prophylactic compartment 118.

The lubricant compartment 116 can be trapezoidally shaped and preferably can comprise a neck 126. The neck 126 facilitates the dispensing of the lubricant 120 from the lubricant compartment 116 by funneling the lubricant 120 through a focused opening. Preferably, the sealed package 102 comprises a weakened section 128 for opening the lubricant compartment 116. The weakened section 128 can be comprised of, but not limited to, a slit, a "V"-shaped indentation, or a small perforation. The weakened section 128 can be located near the neck 126 of the lubricant compartment 116 such that the neck 126 is exposed when the sealed package 102 is torn at the weakened section 128, or can be located anywhere on the sealed package 102 that facilitates dispensing of the lubricant 120.

Preferably the front wall 112 is substantially transparent and is comprised of, but not limited to, a burstable polyester film, a plastic covering, or any other substantially transparent, flexible, polymeric material. A substantially transparent material is desirable because the contents of the sealed package 102 can be seen without having to open it. It is also desirable that the front wall 112 be sufficiently thin, i.e. sufficiently small in thickness, that it is burstable by hand. For example, the front wall 112 can be about 0.004 inches thick. Preferably the rear wall 114 can be substantially opaque and is comprised of, but not limited to, aluminum, paper, or any other opaque material. The rear wall 114 can be about 0.006 inches thick. An opaque material is desirable so that markings on the sealed package 102 can be seen. Both the front wall 112 and the rear wall 114 can comprise markings. Additionally, both the front wall 112 and rear wall 114 can be transparent, and both the front wall 112 and rear wall 114 can be opaque, or the front wall 112 can be transparent and the rear wall 114 can be opaque and vice versa.

So the package 102 can conveniently fit into a wallet, preferably it is about 0.1 to about 0.3 inch in thickness, and more preferably 0.2; preferably about 2 to about 2.6 inches in thickness and more preferably about 2.3 inches; and preferably about 3 to about 4 inches in length, and more preferably about 3.6 inches. These dimensions allow the package to fit into a wallet, but provide sufficient capacity for a single condom and an adequate amount of lubricant.

The top edge 104 and bottom edge 106 are shown in FIG. 1 as having broken perforations that can results when the package 102 is separated from another package, as is possible in the versions shown in FIGS. 1-3. However, this is optional, and when the packages 102 are produced as single discrete units, typically there are no perforations.

Referring now to FIG. 3, a dispensing system 300 comprising a plurality of the sealed packages 102 connected together in the form of a substantially rectangular sheet. The term "rectangular" includes "square." The sealed packages 102 are proximate to each other such that there is a mid package 102a connected at its top edge 104 to a first adjoining package 102b at the bottom edge 106 of the first adjoining package 102b, and at its bottom edge 106 to a second adjoining package 102c at the top edge 106 of the second adjoining package 102c. Any of the sealed packages 102 can serve as a mid package 102a and/or an adjoining package 102b, 102c. The sealed packages 102 are separated by perforations 124b so that each sealed package 102 can be removed from the sheet one at a time or in a group of more than one package 102.

Optionally, different colored prophylactics 122a, 122b, 122c, 122d, 122e can be used. For example, prophylactic 122a can be green, prophylactic 122b can be yellow, prophylactic 122c can be purple, prophylactic 122d can be blue, and prophylactic 122e can be orange. Additionally, the prophylactics 122a, 122b, 122c, 122d, 122e can be a condom of any size, shape, or color, including but not limited to, lubricated, non-lubricated, ribbed, scented, flavored, or colored condoms. Different colors can be used for coding different types of condoms, such as by size, lubricant or no lubricant, thickness, scent, and/or ribs.

Referring now to FIG. 4, a dispensing system 400 comprising a plurality of the sealed packages 102 connected together in the form of a substantially rectangular sheet. The term "rectangular" includes "square." The sealed packages 102 are proximate to each other such that there is a mid package 102d connected at its top edge 104 to a first adjoining package 102e at the bottom edge 106 of the first adjoining package 102e, and at its bottom edge 106 to a second adjoining package 102f at the top edge 106 of the second adjoining package 102f. Any of the sealed packages 102 can serve as a mid package 102d and/or an adjoining package 102e, 102f. The sealed packages 102 are separated by perforations 124b so that each sealed package 102 can be stripped off one at a time.

The lubricant compartment 116 optionally comprises at least two sub-compartments 116a, 116b, with each sub-compartment 116a, 116b comprising a neck 126a, 126b. One of the sub-compartments 116b optionally contains a germicide. In other versions, the sub-compartments 116a, 116b can contain various liquids or gels, including, but not limited to, spermicide, massage oil, flavored liquid, or scented liquid. Therefore, it is understood that the term "lubricant compartment" means that various other liquids and/or gels can be contained within the compartment in addition to lubricant. Additionally, the sealed packages 102 can comprise weakened sections 128a, 128b for opening the sub-compartments 116a, 116b. The weakened sections 128a, 128b can be comprised of, but not limited to, a slit, a "V"-shaped indentation, or a small perforation. The weakened sections 128a, 128b can be located near the necks 126a, 126b of the sub-compartments 116a, 116b such that the necks 126a, 126b are exposed when the sealed packages 102 are torn at the weakened sections 128a, 128b, or can be located anywhere on the sealed packages 102 that facilitates dispensing of the contents of the sub-compartments 116a, 116b.

Referring now to FIG. 5, a system 500 comprising a plurality of sealed packages 102 connected together in the form of a substantially rectangular sheet. The term "rectangular" includes "square." The sealed packages 102 are proximate to each other such that there is a mid package connected to at least two adjoining packages. Any of the sealed packages 102 can serve as a mid package and/or an adjoining package. The sealed packages 102 are separated by perforations 124b so that each sealed package 102 can be stripped off one at a time.

In another version of the invention, the sealed packages 102 are proximate to each other such that there is a mid package 102g connected at its first side edge 108 to a first adjoining package 102h at one of the side edges of the first adjoining package 102h, and at its second side edge 110 to a second adjoining package 102i at one of the side edges of the second adjoining package 102i.

Although the present invention has been discussed in considerable detail with reference to certain preferred embodiments, other embodiments are possible. For example, the front wall 112 may be comprised of multiple different layers, or the sealed package of FIG. 1 can be packaged back-to-back. Therefore, the scope of the appended claims should not be limited to the description of preferred embodiments contained in this disclosure.

All the features disclosed in this specification (including any accompanying claims, abstract, and drawings) can be replaced by alternative features serving the same, equivalent or similar purpose, unless each feature disclosed is one example only of a generic series of equivalent or similar features.

What is claimed is:

1. A dispensing system comprising:
    a) a sealed package having a top edge, a bottom edge, a first side edge, a second side edge, a front wall, and a rear wall;
    b) a first compartment comprising:
        (i) a first sub-compartment containing a lubricant;
        (ii) a second sub-compartment containing a material selected from the group consisting of a germicide, a spermicide, massage oil, flavored liquid, and scented liquid,
    wherein the first sub-compartment and the second sub-compartment are side by side;
        (iii) the first sub-compartment comprising a first neck that is shaped to facilitate dispensing of lubricant from the first sub-compartment, the first neck extending laterally towards the first side edge;
        (iv) the second sub-compartment comprising a second neck that is shaped to facilitate dispensing of material from the second sub-compartment, the second neck extending laterally towards the second side edge;
        (v) a first weakened section at the top edge proximate to but spaced apart from the first neck and located so that by pulling downwardly the first neck is accessed for dispensing lubricant from the first sub-compartment; and
        (vi) a second weakened section at the top edge proximate to but spaced apart from the second neck and located so that by pulling downwardly the second neck is accessed for dispensing material from the second sub-compartment; and
    c) a second compartment containing a prophylactic.

2. The system of claim 1, where the top edge and the bottom edge are ridged.

3. The system of claim 1, where the top edge and the bottom edge are smooth.

4. The system of claim 1, where the first compartment, the second compartment, or both the first compartment and the second compartment are burstable.

5. The system of claim 1, where only the second compartment is burstable.

6. The system of claim 1, where the sealed package comprises dimensions to fit into a user's wallet.

7. The system of claim 1, where the sealed package comprises perforations separating the first compartment from the second compartment.

8. The system of claim 1, where the front wall is substantially transparent.

9. The system of claim 1, where the front wall material is selected from the group consisting of a burstable polyester film, a plastic covering, and substantially transparent, flexible, polymeric material.

10. The system of claim 1, where second compartment is 0.2 inches thick.

11. The system of claim 1, where the second sub-compartment contains a germicide.

12. The system of claim 1, wherein the prophylactic contained in the second compartment is lubricated.

13. The system of claim 1, where a plurality of the sealed packages are connected together in the form of a substantially rectangular sheet, and where the sealed package is no greater than 0.3 inches thick.

14. The system of claim 13, where the sealed packages are proximate to each other such that there is a mid package connected at a top edge to a first adjoining package at a bottom edge of the first adjoining package, and the bottom edge to a second adjoining package at a top edge of the second adjoining package.

15. The system of claim 13, where the sealed packages are proximate to each other such that there is a mid package connected at a top edge to a first adjoining package at a bottom edge of the first adjoining package, and at the bottom edge to a second adjoining package at a top edge of the second adjoining package.

* * * * *